United States Patent [19]
Rayle et al.

[11] Patent Number: 5,922,916
[45] Date of Patent: Jul. 13, 1999

[54] PROCESS TO CHLOROKETOAMINES USING CARBAMATES

[75] Inventors: Heather Lynnette Rayle, North Wales; Renee Caroline Roemmele, Maple Glen; Randall Wayne Stephens, Perkasie; Joshua Anthony Chong, Lansdale; Fereydon Abdesaken, Dresher; Charles Chao Wu, North Wales, all of Pa.

[73] Assignee: Rohm and Haas Company, Philadelphia, Pa.

[21] Appl. No.: 09/058,827

[22] Filed: Apr. 13, 1998

Related U.S. Application Data

[60] Provisional application No. 60/043,554, Apr. 15, 1997.
[51] Int. Cl.⁶ .................................................. C07G 209/36
[52] U.S. Cl. ............................................ 564/487; 548/229
[58] Field of Search .............................. 564/487; 548/229

[56] References Cited

FOREIGN PATENT DOCUMENTS 1 164 411  3/1962  Germany .

*Primary Examiner*—Brian M. Burn
*Attorney, Agent, or Firm*—Charles R. Carpenter

[57] ABSTRACT

The present invention relates to a process for preparing 5-methylene cyclic carbamates either by cyclization of an alkynyl amine with carbon dioxide in the presence of a copper catalyst or by forming an isocyanate from a substituted acetoacetamide followed by hydrolysis. The 5-methylene cyclic carbamates by either method are converted to 5-(chloromethylene) cyclic carbamates, using trichloroisocyanuric acid, followed by hydrolysis to a chloroketoamine.

The chloroketoamine from the process of this invention additionally can be reacted with an organic acid chloride to form an amide compound which is useful as a fungicide.

35 Claims, No Drawings

PROCESS TO CHLOROKETOAMINES USING CARBAMATES

This is a Application of the Provisional Application Ser. No. 60/043,554 filed Apr. 15, 1997.

This invention relates to a novel, inexpensive process to prepare a 5-methylene cyclic carbamate, either from a substituted alkynyl amine and carbon dioxide or from a substituted acetoacetamide via the Hofmann rearrangement. The 5-methylene cyclic carbamate is then chlorinated to a 5-chloromethylene cyclic carbamate using a convenient chlorinating agent followed by hydrolysis to a substituted α-chloroketoamine. The substituted α-chloroketoamine can then be converted to a substituted amide compound which is useful as a fungicide.

There are several problems in the existing field which the present invention successfully overcomes. Previously disclosed routes to the desired 5-methylene cyclic carbamate involve reaction of an acetylenic amine with carbon dioxide at elevated pressure and elevated temperature. Such conditions require expensive equipment and thus limit the commercial value of such a process.

The subsequent preparation of an α-chloroketoamine from the resulting 5-methylene cyclic carbamate by the known and usual methods, such as by using chlorine gas or N-chlorosuccinimide as the chlorinating agent, is also problematic because of a lack of selectivity for monochlorination; both underchlorinated and overchlorinated ketones are typically formed in addition to the desired monochloroketoamine after hydrolysis of the 5-chloromethylene cyclic carbamate. Furthermore, the use of chlorine presents hazards and an equipment expense well known to those skilled in the art.

We have discovered two convenient routes to 5-methylene cyclic carbamates. The first involves the reaction of an alkynyl amine with carbon dioxide in the presence of a copper salt under mild temperature and pressure conditions. The second involves multiple alkylation of an acetoacetamide, formation of an isocyanate using Hofmann reaction conditions, and then cyclization to the 5-methylene cyclic carbamate under acidic conditions. Furthermore, we have identified a novel chlorination reagent, trichloroisocyanuric acid (TCIA), which chlorinates the resulting 5-methylene cyclic carbamate selectively to give a monochlorinated intermediate which, upon acid-catalyzed hydrolysis, affords the desired α-monochloroketoamine selectively and in high yield. TCIA is a high melting, easily handleable solid which can be utilized in extremely precise amounts in order to avoid under- or over- chlorination of the desired material. Although TCIA is a well known, inexpensive and commercially available compound used in the chlorination of swimming pool water and the disinfection of drinking water, its use as a convenient and selective chlorination agent for 5-methylene cyclic carbamates had not been disclosed before this time. An additional feature of this invention provides a convenient process for the selective formation of α,α-dichloroketoamines. The resulting mono- or dichloroketoamine may be reacted with an organic acid chloride to form an amide compound which is useful as a fungicide.

DE 1,164,411 describes a process for the preparation of 5-methyleneoxazolidones-(2) from acetylene amines and carbon dioxide at elevated pressure and temperature in the presence of copper salts. However, the mild conditions employed as part of this invention are not disclosed or suggested. Additionally, neither any utility of these 5-methyleneoxazolidones-(2) nor any subsequent chlorination to form a 5-chloromethylene cyclic carbamate is suggested.

One embodiment of this invention provides a convenient process to α-chloroketoamines, which are useful as intermediates leading to amide fungicides, comprising the steps of cyclizing a substituted alkynyl amine using carbon dioxide in the presence of a copper (I) salt catalyst with moderate temperature and pressure to form a 5-methylene cyclic carbamate in a first step, chlorinating the 5-methylene cyclic carbamate in a solvent using trichloroisocyanuric acid to produce a chlorinated cyclic carbamate intermediate in a second step, and subsequently hydrolyzing the chlorinated cyclic carbamate intermediate with a strong acid to produce the desired α-chloroketoamine in a third step. The resulting α-chloroketoamine can be further reacted with an organic acid chloride to form an amide compound which is useful as a fungicide.

Specifically, this embodiment provides a process for the preparation of an α-chloroketoamine compound of formula (I) comprising the steps of (i) cyclizing an alkynyl amine of formula (II) using carbon dioxide in the presence of a copper (I) salt catalyst with moderate temperature and a pressure of up to 3 atmospheres absolute to form a 5-methylene cyclic carbamate of formula (III)

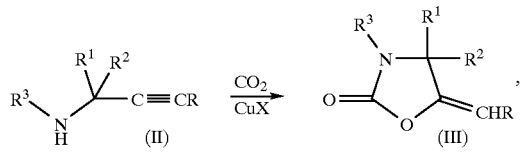

(ii) chlorinating the 5-methylene cyclic carbamate of formula (III) in a solvent using trichloroisocyanuric acid to produce a chlorinated cyclic carbamate intermediate of formula (IV)

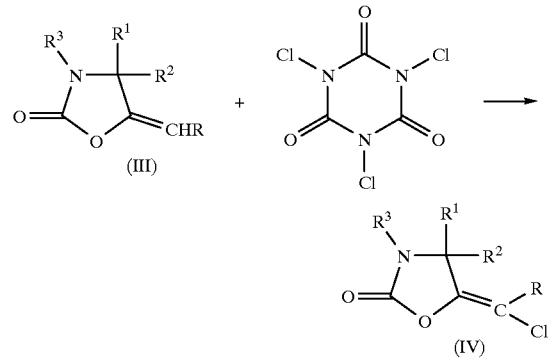

and (iii) hydrolyzing the chlorinated cyclic carbamate intermediate of formula (IV) with an acid to produce the desired monochloroketoamine of formula (I)

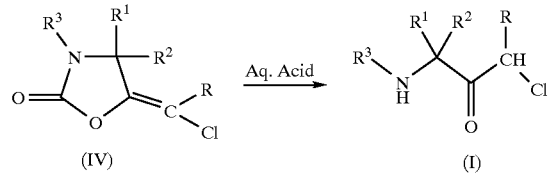

wherein
R and $R^3$ are each independently a hydrogen atom or alkyl,
$R^1$ and $R^2$ are each independently an alkyl or substituted alkyl group, or $R^1$ and $R^2$ together with the carbon atom to which they are attached form a cyclic structure, and X is halo.

In a preferred form of this embodiment,

R and $R^3$ are each independently a hydrogen atom or a $(C_1–C_4)$alkyl, $R^1$ and $R^2$ are each independently a $(C_1–C_4)$alkyl or $R^1$ and $R^2$ together with the carbon atom to which they are attached form a cyclopentyl or cyclohexyl ring, and X is chloro.

In a more preferred form of this embodiment,

R and $R^3$ are each independently a hydrogen atom, methyl or ethyl, and $R^1$ and $R^2$ are each independently methyl or ethyl or $R^1$ and $R^2$ together with the carbon atom to which they are attached form a cyclohexyl ring.

In an even more preferred form of this embodiment,

R and $R^3$ are each a hydrogen atom, and $R^1$ and $R^2$ are each independently methyl or ethyl.

A second embodiment of this invention provides a convenient process to α-chloroketoamines, which are useful as intermediates leading to amide fungicides, comprising the steps of alkylating an optionally substituted acetoacetamide with a first alkyl halide or substituted alkyl halide in the presence of a base in a first step, alkylating the resulting first alkylated acetoacetamide with a second alkyl halide or substituted alkyl halide in the presence of a base in a second step, reacting the resulting twice alkylated acetoacetamide with a hypochlorite compound to form an isocyanate in a third step using Hofmann reaction conditions, cyclizing the resulting isocyanate using an acid to form a 5-methylene cyclic carbamate in a fourth step, chlorinating the 5-methylene cyclic carbamate in a solvent using trichloroisocyanuric acid to produce a chlorinated cyclic carbamate intermediate in a fifth step, and subsequently hydrolyzing the chlorinated cyclic carbamate intermediate with a strong acid to produce the desired α-chloroketoamine in a sixth step. The resulting α-chloroketoamine can be further reacted with an organic acid chloride to form an amide compound which is useful as a fungicide.

Specifically, this embodiment provides a process for the preparation of an α-chloroketoamine compound of formula (I) comprising the steps of (i) alkylating an acetoacetamide of formula (V) to form a first alkylated acetoacetamide of formula (VI)

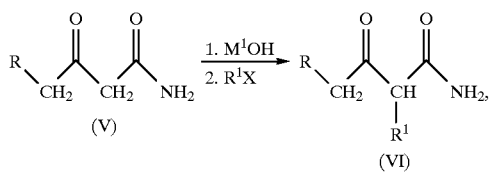

(ii) alkylating the first alkylated acetoacetamide of formula (VI) to form a twice alkylated acetoacetamide of formula (VII)

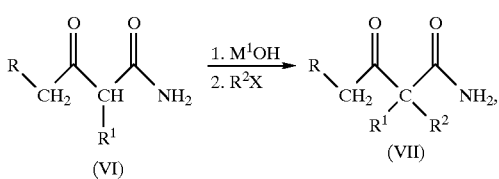

(iii) reacting the twice alkylated acetoacetamide of formula (VII) with a hypochlorite to form an isocyanate of formula (VIII)

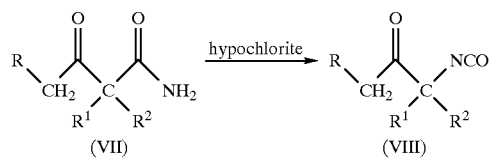

(iv) cyclizing the resulting isocyanate of formula (VIII) using an acid to form a 5-methylene cyclic carbamate of formula (III)

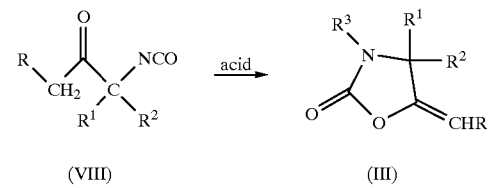

(v) chlorinating the 5-methylene cyclic carbamate of formula (III) in a solvent using trichloroisocyanuric acid to produce a chlorinated cyclic carbamate intermediate of formula (IV)

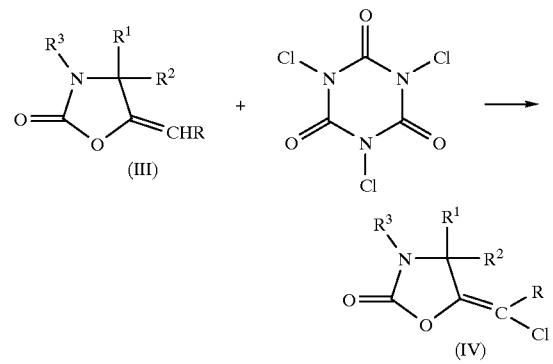

and (vi) hydrolyzing the chlorinated cyclic carbamate intermediate of formula (IV) with an acid to produce the desired monochloroketoamine of formula (I)

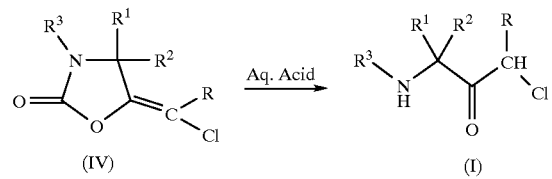

wherein

R is a hydrogen atom or alkyl, $R^1$ and $R^2$ are each independently an alkyl or substituted alkyl group, $R^3$ is a hydrogen atom, $M^1$ is lithium, potassium or sodium, X is halo, and the hypochlorite is selected from the group consisting of calcium hypochlorite, sodium hypochlorite, potassium hypochlorite, lithium hypochlorite and tert-butyl hypochlorite.

In a preferred form of this embodiment,

R is a hydrogen atom or a $(C_1-C_4)$alkyl, $R^1$ and $R^2$ are each independently a $(C_1-C_4)$alkyl, X is chloro, bromo or iodo, and the hypochlorite is calcium hypochlorite or tert-butyl hypochlorite.

In a more preferred form of this embodiment,

R is a hydrogen atom, methyl or ethyl, $R^1$ and $R^2$ are each independently methyl or ethyl and the hypochlorite is calcium hypochlorite.

In an even more preferred form of this embodiment,

R is a hydrogen atom, and $R^1$ and $R^2$ are each independently methyl or ethyl.

In a second aspect of this embodiment, steps (i) and (ii) may be combined into a single step when $R^1$ and $R^2$ are the same alkyl group or $R^1$ and $R^2$ together with the carbon atom to which they are attached form a cyclic structure. Preferred groups when $R^1$ and $R^2$ are the same alkyl group are methyl and ethyl. Preferred reactants in step (i) when $R^1$ and $R^2$ together with the carbon atom to which they are attached form a cyclic structure are X—$(CH_2)_y$—X wherein y is 4 or 5 and X is halo.

In both embodiments of this invention, the amount of TCIA which is employed in the chlorination step may be advantageously increased when the R group of the 5-methylene cyclic carbamate of formula (III) is a hydrogen atom in order to form 5-(dichloromethylene) cyclic carbamates which are subsequently hydrolyzed to α,α-dichloroketoamines which also are useful as intermediates for the preparation of amide fungicides. Specifically, this feature of this invention provides a process for the preparation of an α,α-dichloroketoamine compound of formula (IA) comprising the steps of (ia) forming a 5-methylene cyclic carbamate of formula (III) by cyclizing an alkynyl amine of formula (II) using carbon dioxide in the presence of a copper (I) salt catalyst as described previously

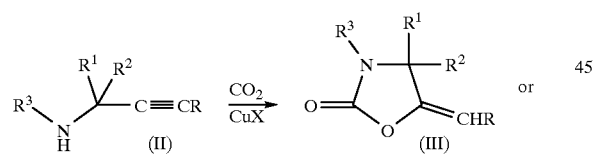

(ib) forming a 5-methylene cyclic carbamate of formula (III) by cyclizing an isocyanate of formula (VIII) using an acid as described previously

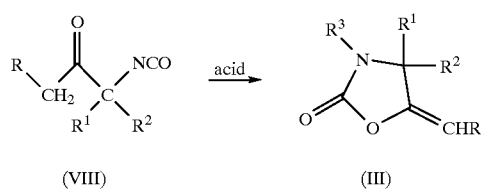

(ii) chlorinating the 5-methylene cyclic carbamate of formula (III) in a solvent using trichloroisocyanuric acid to produce a dichlorinated cyclic carbamate intermediate of formula (IVA)

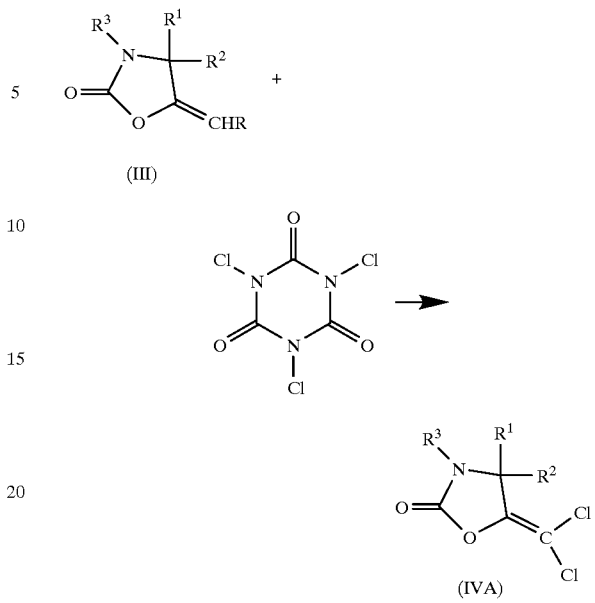

and (iii) hydrolyzing the dichlorinated cyclic carbamate intermediate of formula (IVA) with an acid to produce the desired dichloroketoamine of formula (IA)

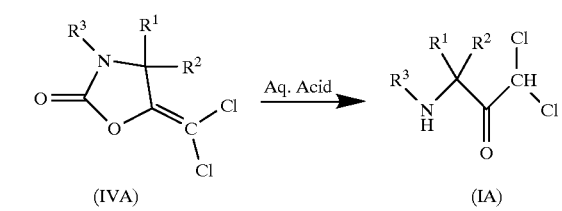

wherein

R is a hydrogen atom, $R^3$ is a hydrogen atom or alkyl, $R^1$ and $R^2$ are each independently an alkyl or substituted alkyl group, or $R^1$ and $R^2$ together with the carbon atom to which they are attached form a cyclic structure, and X is halo.

In a preferred form of this embodiment, $R^3$ is a hydrogen atom or a $(C_1-C_4)$alkyl, $R^1$ and $R^2$ are each independently a $(C_1-C_4)$alkyl or $R^1$ and $R^2$ together with the carbon atom to which they are attached form a cyclopentyl or cyclohexyl ring, and X is chloro.

In a more preferred form of this embodiment, $R^3$ is a hydrogen atom, methyl or ethyl, and $R^1$ and $R^2$ are each independently methyl or ethyl or $R^1$ and $R^2$ together with the carbon atom to which they are attached form a cyclohexyl ring.

In an even more preferred form of this embodiment, $R^3$ is a hydrogen atom, and $R^1$ and $R^2$ are each independently methyl or ethyl.

In both embodiments of this invention, the resulting chloroketoamine of formula (I) or (IA) may be reacted with an organic acid chloride of formula (IX) in the presence of a base to form a fungicidal amide compound of formula (X)

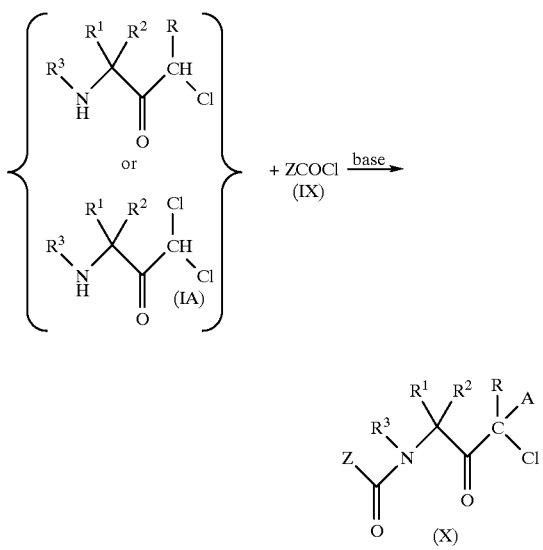

wherein

A is chloro or a hydrogen atom,

Z is alkyl or substituted alkyl, aryl or substituted aryl, heteroaryl or substituted heteroaryl or phenylene, R and $R^3$ are each independently a hydrogen atom or alkyl, and $R^1$ and $R^2$ are each independently an alkyl or substituted alkyl group, or $R^1$ and $R^2$ together with the carbon atom to which they are attached form a cyclic structure.

In a preferred form of this embodiment,

A is a hydrogen atom,

Z is $(C_1-C_8)$alkyl, phenyl or phenyl substituted with up to three substituents independently selected from the group consisting of halo, $(C_1-C_4)$alkyl, $(C_1-C_4)$alkoxy, $(C_2-C_6)$alkynyl, nitro and cyano, 2-naphthyl, 3-pyridyl and 1,4-phenylene, R is a hydrogen atom or a $(C_1-C_4)$alkyl, and $R^1$ and $R^2$ are each independently a $(C_1-C_4)$alkyl or $R^1$ and $R^2$ together with the carbon atom to which they are attached form a cyclopentyl or cyclohexyl ring.

In a more preferred form of this embodiment,

Z is 3-heptyl, phenyl, 4-halophenyl, 2,6-dihalophenyl, 4-$(C_1-C_4)$alkylphenyl, 3,5-dihalophenyl, 3,5-di$(C_1-C_4)$alkylphenyl, 4-$(C_1-C_4)$alkyl-3,5-dihalophenyl, 4-cyano-3,5-dihalophenyl, 4-$(C_1-C_4)$alkoxy-3,5-dihalophenyl, 4-nitrophenyl, 2-naphthyl, 3-pyridyl or 1,4-phenylene, R and $R^3$ are each independently a hydrogen atom, methyl or ethyl, and $R^1$ and $R^2$ are each independently methyl or ethyl or $R^1$ and $R^2$ together with the carbon atom to which they are attached form a cyclohexyl ring.

In an even more preferred form of this embodiment,

Z is 4-chlorophenyl, 2,6-difluorophenyl, 3,5-dimethylphenyl, 3,5-dichloro-4-methylphenyl, 4-nitrophenyl, 1,4-phenylene, 2-naphthyl, 3-pyridyl or 3-heptyl, R and $R^3$ are each a hydrogen atom, and $R^1$ and $R^2$ are each independently methyl or ethyl.

In this invention, alkyl means a $(C_1-C_8)$ straight or a $(C_3-C_8)$ branched chain alkyl group and includes, for example, methyl, ethyl, n-propyl, isopropyl, n-butyl, isobutyl, sec-butyl, tert-butyl, n-amyl, isoamyl, n-hexyl, isooctyl and the like. Substituted alkyl means an alkyl substituted with one or more substituents selected from the group consisting of alkoxy, halo, alkylthio and cyano.

Alkoxy means a $(C_1-C_4)$ straight or a $(C_3-C_4)$ branched chain alkyl group attached to an oxygen atom, for example, methoxy, ethoxy, isobutoxy and the like.

Alkylthio means a $(C_1-C_4)$ straight or a $(C_3-C_4)$ branched chain alkyl group attached to an sulfur atom, for example, methylthio, n-propylthio, sec-butylthio and the like.

Halo means bromo, chloro, fluoro and iodo.

Aryl means phenyl, naphthyl, or phenyl or naphthyl substituted with one to three substituents independently selected from the group consisting of halo, alkyl, alkynyl, alkoxy, nitro or cyano. Examples include, but are not limited to, phenyl, 2-naphthyl, 4-nitrophenyl, 4-chlorophenyl, 3,5-dimethylphenyl, 2,6-difluorophenyl, 3,5-dichloro-4-methylphenyl, 3,5-dichlorophenyl, 3,5-difluorophenyl, 3,5-dibromophenyl, 3-chloro-4-ethyl-5-fluorophenyl, 3,5-dichloro4-cyanophenyl, 3,5-dichloro-4-methoxyphenyl, 3,5-difluoro-4-propargylphenyl, 3,5-dibromo-4-methylphenyl and the like.

Alkynyl means a $(C_2-C_6)$alkynyl, for example, ethynyl, propargyl, 2-hexynyl and the like.

Heteroaryl means a 5-membered aromatic ring which may contain an oxygen atom, a sulfur atom, 1, 2 or 3 nitrogen atoms, an oxygen atom with 1 or 2 nitrogen atoms or a sulfur atom with 1 or 2 nitrogen atoms, or a 6-membered aromatic ring containing 1, 2 or 3 nitrogen atoms, or heteroaryl substituted with up to two substituents selected from halo, alkyl, haloalkyl or cyano. Examples include, but are not limited to 2-furyl, 2-thienyl, 4-chloro-2-thienyl, 2-oxazolyl, 2-imidazolyl, 1,2,4-triazol-1-yl, 2-imidazolyl, 2-pyrrolyl, 2-pyridyl, 3-pyridyl, 4-pyridyl, 4-pyridazinyl, 4-pyrimidinyl, 2-pyrazinyl, 1,3,5-triazin-2-yl, 4-chloro-3-pyridyl and the like.

Phenylene means 1,4-phenylene.

Although a specific isomer is shown throughout for the compound of formula (IV), it is to be understood that formula (IV) actually represents a mixture of the cis and trans isomeric forms.

In the first embodiment of this invention, the cyclization step to form a 5-methylene cyclic carbamate from an alkynyl amine can be run from about −20° C. to about 35° C. for from about 6 hours to several days. A preferred temperature is from about 0° C. to about 25° C. A more preferred temperature is from about 10° C. to about 25° C. The copper salt catalyst is present in from about 1 mole % to about 10 mole %, based on the starting alkynyl amine, and the carbon dioxide can be in excess or added in portions to maintain a $CO_2$ starved system. An excess of $CO_2$ is usually preferred. The reaction can be run with or without a solvent. A preferred copper salt catalyst is copper (I) chloride or copper (I) iodide. A more preferred copper salt is copper (I) chloride. When a solvent is used, a polar solvent is preferred. A preferred polar solvent is methyl tert-butyl ether. If the reaction is run under carbon dioxide starved conditions, a significant amount, up to ~20%, of a higher molecular weight, dimeric by-product can be obtained as well as about 5–10% of a ring opened isocyanate. However, using an excess of $CO_2$ will greatly minimize this problem. The reaction can be run using an atmospheric pressure of $CO_2$ or, alternatively, a moderate pressure from about 1 to about 3 atmospheres absolute may be used. The carbon dioxide can be bubbled through a solvent containing the catalyst until the solvent reaches saturation and the amine can then be added slowly to the reaction. Alternatively, carbon dioxide can be added, either as a solid or bubbled in as a gas, to a solution of the amine and catalyst. In both cases, either a batch or a continuous process may be used. The product can be isolated using standard workup procedures, such as quenching with water, acidification if necessary, extracting and washing, drying the organic layer, evaporation of the solvent, and recovery by distillation. The product can be isolated usually with a purity of from 85–98%.

In the second embodiment of this invention, a base, preferably NaOH or KOH, is added to a solution of an acetoacetamide in a polar solvent. It is preferred that the polar solvent is a water soluble one such as methanol. After mixing, the first alkylating agent, preferably an alkyl halide, is added to the solution at a temperature of from about 0° C. to about 50° C. The stoichiometry, reaction time and temperature are somewhat dependent on the alkylating agent employed; for example alkyl iodides tend to be more facile alkylating agents than the bromides or chlorides. Usually, a relatively small excess of alkylating agent is used. The first alkylated acetoacetamide either can be isolated in preparation for reaction with a second alkylating agent under similar conditions or the second alkylating agent can be added directly to the first alkylated acetoacetamide solution. The steps may be advantageously combined when the two alkyl groups are the same by using at least 2 equivalents of alkylating agent for the acetoacetamide. Similarly, when a ring structure is desired, approximately one equivalent of a dihalopolymethylene alkylating agent, such as 1,4-dibromobutane or 1,5-dibromopentane, is used to alkylate the acetoacetamide.

The twice alkylated acetoacetamide is converted to an isocyanate by using Hofmann reaction conditions. Generally it is most convenient to add the hypochlorite to a solution of the acetoacetamide in a solvent which is inert to the hypochlorite. Suitable solvents include aromatic and aliphatic hydrocarbons or chlorinated aromatic and aliphatic hydrocarbons. A preferred solvent is methylene chloride because of its convenient boiling point. Anhydrous reaction conditions are sought in order to prevent hydrolysis of the isocyanate. Various inorganic hypochlorites, for example, sodium, potassium, lithium or calcium, as well as organic hypochlorites, for example, tert-butyl, effect the reaction. Preferred hypochlorites include sodium, calcium and tert-butyl hypochlorites. A more preferred hypochlorite is calcium hypochlorite. The amount of hypochlorite employed is generally from about 0.1 to about 2.0 equivalents per equivalent of acetoacetamide. A preferred amount of hypochlorite is from about 0.5 to about 1.5 equivalents. A more preferred amount is from about 0.8 to about 1.4 equivalents.

The isocyanate is cyclized to the 5-methylene cyclic carbamate by contacting it with an acid such as acetic acid, trifluoroacetic acid or a Nafion® resin, a polymeric perfluorosulfonic acid. The preferred acid is Nafion. The solvents which are used in this step are the same as those employed in the preceding Hofmann reaction. The reaction temperature is usually from about 0° C. to about 50° C.

In both the embodiments of this invention, the chlorination step of the 5-methylene cyclic carbamate using TCIA may be performed at a temperature of from about −30° to about 100° C. A preferred chlorination temperature is from about 0° to 70° C. More preferred in order to obtain the best chlorination selectivity is a temperature of about 50° C. or lower. Even more preferred is a temperature from 0° to 30° C. The reaction is not pressure-dependent, but a pressure of 1 atmosphere is usually preferred for convenience. The stoichiometry of the reagents is extremely important. If less than 0.333 equivalent of TCIA per equivalent of 5-methylene cyclic carbamate is used, some of the 5-methylene cyclic carbamate starting material will remain unreacted. If greater than 0.333 equivalent is used, an overchlorinated intermediate is formed that leads to a dichloroketoamine after hydrolysis. However, as noted previously, an added feature of this invention provides for the convenient formation of a 5-(dichloromethylene) cyclic carbamate and subsequent formation of an α,α-dichloroketoamine when ≧0.667 equivalent of TCIA is used per equivalent of the 5-methylene cyclic carbamate in the situation where the methylene group of the cyclic carbamate is not substituted with an alkyl group. The chlorination reaction time can vary from about 5 minutes to about 1 hour and is dependent on both the size and type of reactor equipment employed and the solvent used. The chlorination solvent is usually a polar solvent such as, but not limited to, an ether, an acid, an ester or a ketone, for example ethyl acetate, butyl acetate, acetic acid and methyl t-butyl ether. Preferred polar solvents are acetic acid, ethyl acetate or butyl acetate. Nonpolar solvents such as an aromatic hydrocarbon, for example toluene, an aliphatic hydrocarbon, for example heptane and isooctane, or a chlorinated hydrocarbon, for example methylene chloride, may be also employed. A preferred nonpolar solvent is methylene chloride. After the chlorination reaction is carried out to the desired stage, the cyanuric acid by-product may be removed by filtration and/or by washing with a common base such as aqueous sodium carbonate, sodium hydroxide and the like. The resulting solution containing the 5-chloromethylene cyclic carbamate is then subjected to the hydrolysis step.

For the hydrolysis step, the same solvent that was utilized in the chlorination can be generally used for convenience. The hydrolysis step occurs readily with any strong acid having a pH of about ≦2. Either an aqueous acid or a non-aqueous acid admixed with some water may be employed. A common acid such as, but not limited to, hydrochloric acid, sulfuric acid, trifluoroacetic acid, methanesulfonic acid or toluenesulfonic acid is convenient to use. Aqueous hydrochloric acid, in concentrations of from about 10% to about 37%, or sulfuric acid, in concentrations of from about 10% to about 98%, are preferred. An acidic ion-exchange resin may also be utilized. The hydrolysis step usually takes from about 30 minutes to about 24 hours, with the time depending on the strength of the acid, the temperature and the size and nature of the equipment employed. The pressure used is not critical. However, 1 atmosphere is usually preferred for convenience.

In a typical representative reaction procedure for the chlorination and hydrolysis steps of both embodiments, the cyclic carbamate and solvent are combined and the resulting solution is chilled to 0–5° C. using an ice bath. The TCIA is added gradually, keeping the reaction temperature below 30° C. if possible. Once the TCIA has been added, the resulting slurry is warmed to room temperature and stirred until the reaction is complete based on gas chromatographic (GC) analysis. Most of the cyanuric acid by-product is removed by filtration. The desired acid to be used in the hydrolysis step is added to the filtrate and the mixture is heated for the appropriate time to effect hydrolysis. The solvent is removed in vacuo to give the desired chloroketoamine as a solid.

The chlorinated intermediate is usually a mixture of chlorinated carbamate isomers along with ring opened isocyanate. The ratio varies depending on the experimental conditions, but all these materials hydrolyze to the same chloroketoamine. Isocyanate hydrolyzes more rapidly than the carbamates. Upon standing the isocyanate closes to the carbamate again and an equilibrium is reached which is different for each example. Purity of the final chloroketoamine ranges from about 85 to 98% depending mainly on the purity of starting carbamate and how efficiently the cyanuric acid by-product of the chlorination is removed.

The following examples, tables and experimental procedures are provided for guidance to the practitioner and are not meant to limit the scope of the invention which is defined by the claims.

The examples in Table I were prepared using either Method A or Method B.

TABLE I

EXAMPLES C-1 TO C-6
Formation of Cyclic Carbamates from Alkynyl Amines and Carbon Dioxide

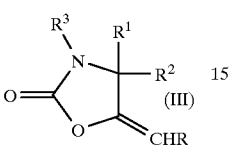

| Ex. No. | R | $R^1$ | $R^2$ | $R^3$ | Method | GC Purity | Yield |
|---|---|---|---|---|---|---|---|
| C-1 | H | $CH_3$ | $C_2H_5$ | H | A | 95% | 48% |
| C-2 | H | $CH_3$ | $C_2H_5$ | H | B | 91% | 70% |
| C-3 | H | $C_2H_5$ | $C_2H_5$ | H | B | 90% | 42% |
| C-4 | H | —$(CH_2)_5$— | | H | A | 99% | 15% |
| C-5 | H | —$(CH_2)_5$— | | H | B | 90% | 21% |
| C-6 | H | $CH_3$ | $CH_3$ | H | A | 99% | 54% |

Method A

Excess $CO_2$ Usage at Atmospheric Pressure

Example C-1

Formation of 4-Ethyl-4-methyl-5-methylene-1,3-oxazolin-2-one

To 30 mL of methyl tert-butyl ether was added 0.38 g (3.9 mmol) of copper (I) chloride. Carbon dioxide was bubbled vigorously through the solution at 0° C. for one hour in order to saturate the solvent. 3-Amino-3-methyl-1-pentyne (10 g, 77 mmol, 75 wt % in water) was added dropwise over 6 h. After addition the reaction was run for 2 h at 0° C. Carbon dioxide was bubbled through the solution constantly. Additional solvent usually needed to be added due to evaporation. When the reaction was complete the solvent was removed in vacuo and the residue partitioned between ethyl acetate and water. The aqueous was extracted three additional times with ethyl acetate before combining the organic phases, drying over sodium sulfate, filtering and evaporating in vacuo to dryness to give the desired product as a light orange low melting solid in 48% yield (5.2 g, 36.8 mmol). Additional product was present in the aqueous phase based on GC analysis and can be recovered by further extraction if desired.

If the starting alkynyl amine was anhydrous, the addition of water was necessary to obtain reasonable reaction rates. Approximately 16 equivalents of water and up to 0.333 equivalent, based on alkynyl amine, of copper (I) halide should be added.

Method B $CO_2$ Starved Reaction

Example C-2

Formation of 4-Ethyl-4-methyl-5-methylene-1,3-oxazolin-2-one

To a round bottom flask equipped with an overhead stirrer, thermometer, reflux condenser and heating mantle was added 50 g (381 mmol) of a 75% aqueous solution of 3-amino-3-methylpentyne, 50 mL of methyl tert-butyl ether and 1.0 g of copper (I) chloride. Solid carbon dioxide was added periodically as pellets through the condenser allowing 10–15 min between additions. After a 7 h reaction time the reaction mixture was transferred to a separatory funnel and diluted with 200 mL of methyl tert-butyl ether. This organic phase was washed with 200 mL of 6% aqueous ammonium hydroxide solution and brine before evaporating to dryness in vacuo to give a 70.6% yield (38 g, 269 mmol) of desired product as a light amber oil that solidified upon standing. The material was 91% pure by GC analysis.

EXAMPLES H-1 TO H-4

Formation of Cyclic Carbamates from Acetoacetamide via the Hofmann Reaction

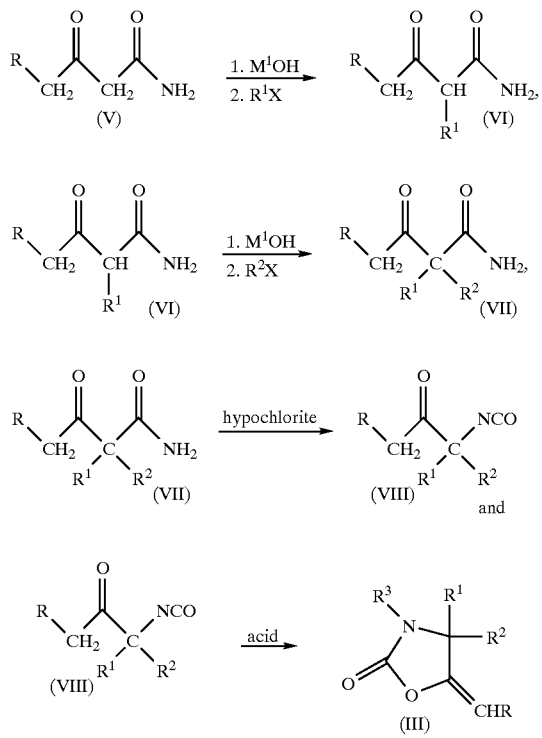

Example H-1

Synthesis of 2,2-Diethlylacetoacetamide

To a 500 mL, 5-necked flask, equipped with a circulating jacket, a thermometer, a nitrogen blanket line atop a condenser, an addition funnel, a syringe pump, and a mechanical stirrer, were charged 50.6 g of acetoacetamide (0.50 mol), 50 mL of deionized water and 50 g of methanol. The mixture was heated to 50° C. and stirred until all solids were dissolved. A 45% aqueous potassium hydroxide solution (136.9 g, 1.10 mol) was then added to the reaction over a period of 5 minutes. The resulting solution was stirred for 30 minutes, then 130.8 g of ethyl bromide (1.20 mol) was added to the mixture through the syringe pump over a period of 30 minutes. Upon the completion of the addition, the mixture was stirred at 50° C. for 4 hours. After this period, all volatiles were removed at 60° C./20 mm Hg. The solid residue was dissolved in 300 mL of water and extracted with chloroform (3×200 mL). After the chloroform was removed in vacuo, 62.4 g of product was obtained. Crude yield: 96.7%.

Example 2-H

Synthesis of 2-Ethyl-2-methylacetoacetamide

To a 500 mL, 5-necked flask, equipped with a circulating jacket, a thermometer, a nitrogen blanket line atop a condenser, an addition funnel, a syringe pump, and a mechanical stirrer, were charged 101.1 g of acetoacetamide (1.00 mol), 100 mL of deionized water and 100 g of methanol. The mixture was stirred at ambient temperature until all solids were dissolved. A 45% aqueous potassium hydroxide solution (99.6 g, 0.80 mol) was then added to the above solution through the addition funnel over a period of 5 minutes. The resulting mixture was stirred for 30 minutes and then cooled to 15° C. Ethyl bromide (130.8 g, 1.20 mol) was added to the mixture through the syringe pump over a period of 30 minutes. The resulting mixture was stirred at 15° C. for 16 hours. All volatiles were then removed at 60° C./20 mmHg. The solid residue was dissolved in 300 mL of water and extracted with chloroform. A total of six chloroform extractions were performed (60 mL+5×200 mL). The first extraction contained a high level of 2,2-diethylacetoacetamide and was discarded. The remaining extraction solutions were combined. After chloroform was removed in vacuo, 67.7 g of 2-ethylacetoacetamide was obtained. Crude yield: 66% (based on KOH charge).

2-Ethylacetoacetamide (21.0 g, 163 mmol) and 50 mL of methanol were charged to a 100 mL, 4-necked flask which was equipped with a thermometer, a nitrogen blanket line atop a condenser, an addition funnel, and a magnetic stirrer. The mixture was stirred until a homogeneous solution was obtained. To the solution was added 14.3 g of 50% aqueous sodium hydroxide solution (179 mmol, 1.1 eq), and the resulting mixture was stirred at ambient temperature for 30 minutes. Methyl iodide (25.4 g, 179 mmol, 1.1 eq) was then added to the reaction mixture through the addition funnel in 30 minutes. Upon the completion of the addition, the reaction mixture was stirred for 14 hours at ambient temperature. After this period, all volatile components were removed at 60° C./20 mmHg. The solid residue was dissolved in 100 mL of water and extracted with ethyl acetate (3×100 mL). After the ethyl acetate was removed in vacuo from the combined extracts, 20.2 g of a white solid was obtained. Crude yield: 87%.

Example 3-H

Hofmann Rearrangement of 2,2-Diethylacetoacetamide

To a 25 mL flask were charged 1.00 g of 2,2-diethylacetoacetamide (6.37 mmol), 2.40 g of $Ca(OCl)_2$ (16.8 mmol), and 15 mL of methylene chloride. The mixture was heated to reflux and stirred under nitrogen for 90 minutes. GC analysis showed that at the end of this period the mixture contained 95% of 3-ethyl-3-isocyanato-2-pentanone.

Example 4-H

Isomerization of 3-Ethyl-3-isocyanato-2-pentanone to Cyclic Carbamate

The reaction mixture from Example 3-H was filtered to remove insoluble materials. To the filtrate was added 1.00 g of Nafion resin (polymeric perfluorosulfonic acid). The resulting suspension was stirred at ambient temperature for 16 hours. GC analysis showed that the 3-ethyl-3-isocyanato-2-pentanone was quantitatively isomerized to the corresponding cyclic carbamate during this period.

TABLE II

EXAMPLES T-1a, 1b, 2 and 3
Formation of Chloroketoamines from Cyclic Carbamates and TCIA

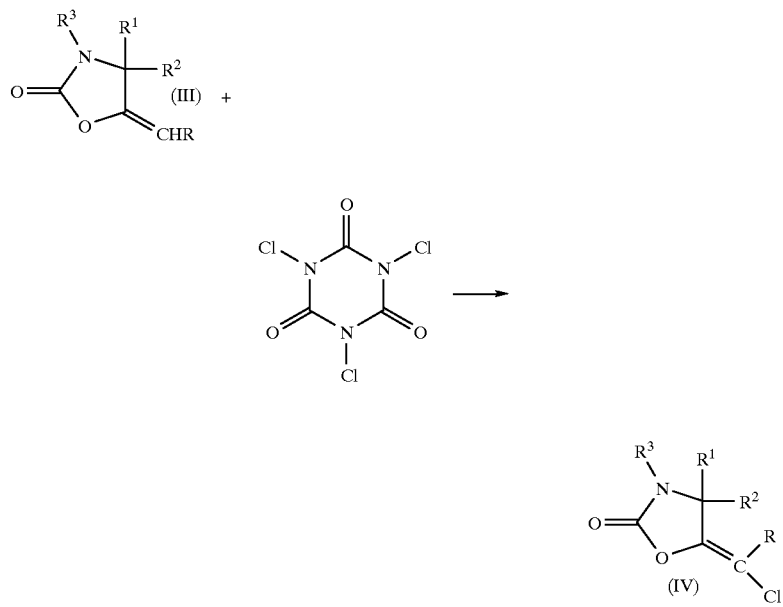

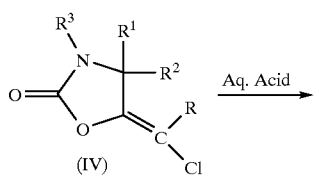

and

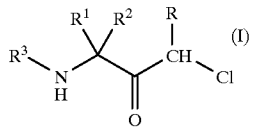

| | Compound | | | | Cholorination | | | Hydrolysis | | |
|---|---|---|---|---|---|---|---|---|---|---|
| Ex. No. | R | R¹ | R² | R³ | Solvent[d] | Yield | Purity | Acid | Yield | Purity |
| T-1a | H | C₂H₅ | CH₃ | H | CH₂Cl₂ | 100% | 85% | conc. H₂SO₄ | 68%[a] | 94% |
| T-1b | H | C₂H₅ | CH₃ | H | AcOH | 88% | 93% | conc. HCl | 100%[a] | 92% |
| T-2 | H | CH₃ | CH₃ | H | EtOAc | 100%[c] | —[e] | conc. HCl | 66.3%[b] | —[e] |
| T-3 | H | —(CH₂)₅— | | H | EtOAc | 100%[c] | —[e] | conc. HCl | 86%[b] | —[e] |

[a]Isolated yield, after workup
[b]GC yield
[c]Crude carried directly to hydrolysis step
[d]Under solvent: AcOH is acetic acid; EtOAc is ethyl acetate
[e]Purity not determined The examples in Table II were obtained using the general procedure for 3-amino-1-chloro-2-methyl-2-pentanone.

General Procedure for the Preparation of 3-Amino-1-chloro-2-methyl-2-pentanone Hydrochloride To 10 g (64 mmol) of 4-ethyl-4-methyl-5-methylene-1,3-oxazin-2-one in 30 mL of solvent at 0° C. was added lowly from a solids addition funnel a total of 4.89 g (21 mmol) of trichloroisocyanuric acid while keeping the reaction temperature below 20° C. Once addition was complete, the reaction was warmed to room temperature where it was allowed to stir for an additional hour or until GC analysis showed the reaction to be complete. If starting material remained after one hour, additional trichloroisocyanuric acid was added as needed based on the GC analysis. Once the reaction was complete, the solids were removed by either vacuum or gravity filtration and the solvent evaporated in vacuo. The residue was then dissolved in 20% hydrochloric acid and heated at 60° C. for 8 hours. The solvent was removed in vacuo to give the desired product in nearly quantitative yield as a solid.

If desired, the residual cyanuric acid can be removed by doing an aqueous base wash of the organic filtrate before the solvent removal using a bicarbonate or carbonate salt solution. When acetic acid was used as the chlorination solvent, a final work up of the amine was required. The workup was also necessary when sulfuric acid was used in the hydrolysis. Water was added to the reaction mixture at 0° C. and the reaction was neutralized to about a pH of 8 using a suitable caustic solution. The aqueous layer was extracted 3 times with dichloromethane. The organic layers were combined and extracted twice with about 10% hydrochloric acid. The acidic extracts were combined and evaporated to dryness in vacuo to give the product as a solid residue. Yields were poorer when a workup is done, typically from 40 to 70% of the desired chloroketoamine. Without a workup, the yields were usually 95–100% in the hydrolysis step. The product may be isolated as the hydrochloride salt or as the free base.

NOTE: 3-Amino-1-chloro-2-methyl-2-pentanone hydrochloride is a skin sensitizing agent and appropriate precautions to avoid dermal exposure should be taken.

It is to be understood that changes and variations in this invention may be made without departing from the spirit and scope of this invention as defined by the appended claims.

We claim:

1. A process for the preparation of an α-chloroketoamine compound of formula (I) comprising the steps of (i) cyclizing an alkynyl amine of formula (II) using carbon dioxide in the presence of a copper (I) salt catalyst with moderate temperature and a pressure of up to 3 atmospheres absolute to form a 5-methylene cyclic carbamate of formula (III)

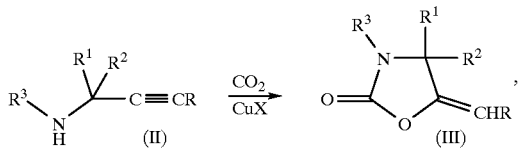

(ii) chlorinating the 5-methylene cyclic carbamate of formula (III) in a solvent using trichloroisocyanuric acid to produce a chlorinated cyclic carbamate intermediate of formula (IV)

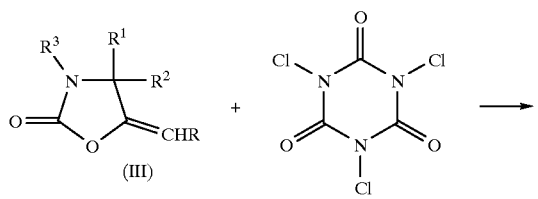

-continued

and (iii) hydrolyzing the chlorinated cyclic carbamate intermediate of formula (IV) with an acid to produce the desired monochloroketoamine of formula (I)

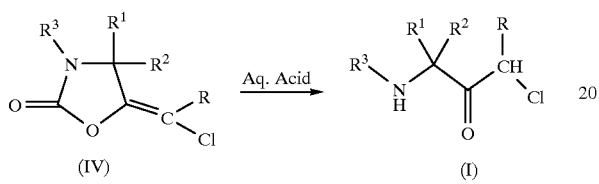

wherein

R and $R^3$ are each independently a hydrogen atom or alkyl, $R^1$ and $R^2$ are each independently an alkyl or substituted alkyl group, or $R^1$ and $R^2$ together with the carbon atom to which they are attached form a cyclic structure, and X is halo.

2. The process of claim 1 wherein

R and $R^3$ are each independently a hydrogen atom or a $(C_1-C_4)$alkyl, $R^1$ and $R^2$ are each independently a $(C_1-C_4)$alkyl or $R^1$ and $R^2$ together with the carbon atom to which they are attached form a cyclopentyl or cyclohexyl ring, and X is chloro.

3. The process of claim 2 wherein

R and $R^3$ are each independently a hydrogen atom, methyl or ethyl, and $R^1$ and $R^2$ are each independently methyl or ethyl or $R^1$ and $R^2$ together with the carbon atom to which they are attached form a cyclohexyl ring.

4. The process of claim 3 wherein

R and $R^3$ are each a hydrogen atom, and $R^1$ and $R^2$ are each independently methyl or ethyl.

5. The process of claim 1 wherein the temperature of step (i) is from $-20°$ C. to $35°$ C.

6. The process of claim 1 wherein an excess of $CO_2$ is used in step (i).

7. The process of claim 1 wherein the copper (I) salt catalyst in step (i) is copper (I) chloride or copper (I) iodide.

8. The process of claim 1 wherein an atmospheric pressure of $CO_2$ is used in step (i).

9. A process for the preparation of an α-chloroketoamine compound of formula (I) comprising the steps of (i) alkylating an acetoacetamide of formula (V) to form a first alkylated acetoacetamide of formula (VI)

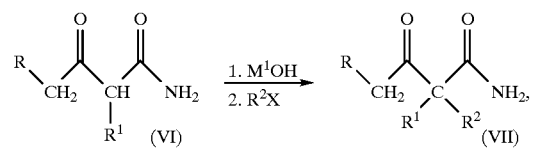

(ii) alkylating the first alkylated acetoacetamide of formula (VI) to form a twice alkylated acetoacetamide of formula (VII)

(iii) reacting the twice alkylated acetoacetamide of formula (VII) with a hypochlorite to form an isocyanate of formula (VIII)

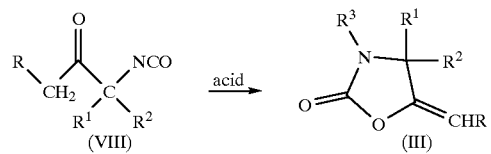

(iv) cyclizing the resulting isocyanate of formula (VIII) using an acid to form a 5-methylene cyclic carbamate of formula (III)

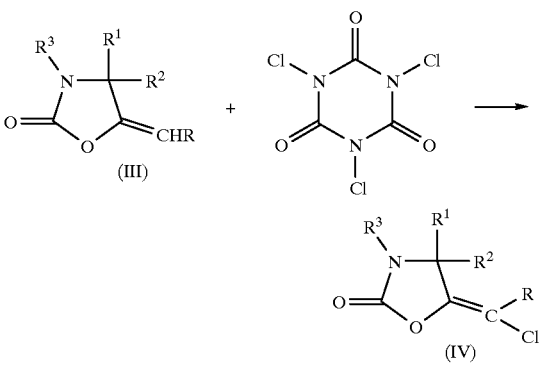

(v) chlorinating the 5-methylene cyclic carbamate of formula (III) in a solvent using trichloroisocyanuric acid to produce a chlorinated cyclic carbamate intermediate of formula (IV)

and (vi) hydrolyzing the chlorinated cyclic carbamate intermediate of formula (IV) with an acid to produce the desired monochloroketoamine of formula (I)

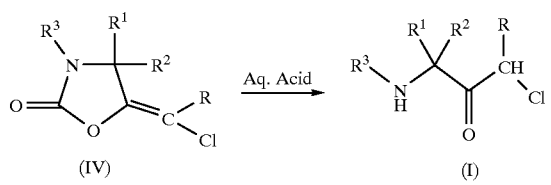

wherein
- R is a hydrogen atom or alkyl,
- $R^1$ and $R^2$ are each independently an alkyl or substituted alkyl group,
- $R^3$ is a hydrogen atom,
- $M^1$ is lithium, potassium or sodium,
- X is halo, and
- the hypochlorite is selected from the group consisting of calcium hypochlorite, sodium hypochlorite, potassium hypochlorite, lithium hypochlorite and tert-butyl hypochlorite.

10. The process of claim 9 wherein
- R is a hydrogen atom or a $(C_1-C_4)$alkyl,
- $R^1$ and $R^2$ are each independently a $(C_1-C_4)$alkyl,
- X is chloro, bromo or iodo, and
- the hypochlorite is calcium hypochlorite or tert-butyl hypochlorite.

11. The process of claim 10 wherein
- R is a hydrogen atom, methyl or ethyl,
- $R^1$ and $R^2$ are each independently methyl or ethyl and
- the hypochlorite is calcium hypochlorite.

12. The process of claim 11 wherein
- R is a hydrogen atom, and
- $R^1$ and $R^2$ are each independently methyl or ethyl.

13. The process of claim 9 wherein steps (i) and (ii) may be combined into a single step when $R^1$ and $R^2$ are the same alkyl group or $R^1$ and $R^2$ together with the carbon atom to which they are attached form a cyclic structure.

14. The process of claim 13 wherein when $R^1$ and $R^2$ are both methyl or are both ethyl.

15. The process of claim 13 wherein $R^1$ and $R^2$ together with the carbon atom to which they are attached form a cyclic structure by reaction of X—$(CH_2)_y$—X with the acetoacetamide wherein y is 4 or 5 and X is halo.

16. A process according to claims 9 or 13 wherein the hypochlorite used in step (iii) is selected from the group consisting of sodium hypochlorite, calcium hypochlorite and tert-butyl hypochlorite.

17. The process of claim 16 wherein the amount of hypochlorite employed is 0.1 to 2.0 equivalents per equivalent of acetoacetamide.

18. A process according to claims 9 or 13 wherein the acid used in step (iv) is acetic acid, trifluoroacetic acid or a polymeric perfluorosulfonic acid.

19. A method of preparing a 5-(chloromethylene) cyclic carbamate or a 3,5-(dichloromethylene) cyclic carbamate by the reaction of a 5-methylene cyclic carbamate with trichloroisocyanuric acid.

20. The method of claim 19 wherein the product is a 5-(chloromethylene) cyclic carbamate.

21. A process according to claims 1 or 9 wherein the chlorination step of the 5-methylene cyclic carbamate using TCIA is performed at a temperature of from −30° C. to 100° C.

22. The process of claim 21 wherein the chlorination temperature is from 0° C. to 70° C.

23. The process of claim 22 wherein the chlorination temperature is 50° C. or lower.

24. The process of claim 21 wherein the chlorination solvent is an ether, an acid, an ester, a ketone, an aromatic hydrocarbon, an aliphatic hydrocarbon, or a chlorinated hydrocarbon.

25. The process of claim 24 wherein the chlorination solvent is ethyl acetate, butyl acetate, acetic acid, methyl t-butyl ether, toluene, heptane, isooctane, or methylene chloride.

26. The process of claim 25 wherein the chlorination solvent is acetic acid, ethyl acetate, butyl acetate, or methylene chloride.

27. A process according to claims 1 or 9 wherein the acid used in the hydrolysis step of the 5-(chloromethylene) cyclic carbamate is selected from the group consisting of hydrochloric acid, sulfuric acid, trifluoroacetic acid, methanesulfonic acid, toluenesulfonic acid, and an acidic ion exchange resin.

28. A process for the preparation of an α,α-dichloroketoamine compound of formula (IA) comprising the steps of
- (ia) forming a 5-methylene cyclic carbamate of formula (III) by cyclizing an alkynyl amine of formula (II) using carbon dioxide in the presence of a copper (I) salt catalyst

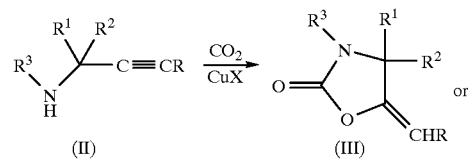

- (ib) forming a 5-methylene cyclic carbamate of formula (III) by cyclizing an isocyanate of formula (VIII) using an acid

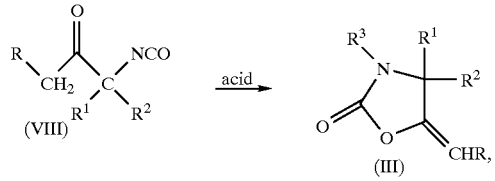

- (ii) chlorinating the 5-methylene cyclic carbamate of formula (III) in a solvent using trichloroisocyanuric acid to produce a dichlorinated cyclic carbamate intermediate of formula (IVA)

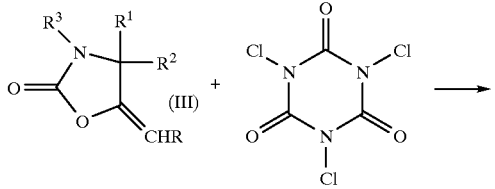

21

-continued (IVA)

and (iii) hydrolyzing the dichlorinated cyclic carbamate intermediate of formula (IVA) with an acid to produce the desired dichloroketoamine of formula (IA)

(IVA) →[Aq. Acid] (IA)

wherein

R is a hydrogen atom, $R^3$ is a hydrogen atom or alkyl, $R^1$ and $R^2$ are each independently an alkyl or substituted alkyl group, or $R^1$ and $R^2$ together with the carbon atom to which they are attached form a cyclic structure, and X is halo.

29. The process of claim 28 wherein $R^3$ is a hydrogen atom or a $(C_1-C_4)$alkyl, $R^1$ and $R^2$ are each independently a $(C_1-C_4)$alkyl or $R^1$ and $R^2$ together with the carbon atom to which they are attached form a cyclopentyl or cyclohexyl ring, and X is chloro.

30. The process of claim 29 wherein $R^3$ is a hydrogen atom, methyl or ethyl, and $R^1$ and $R^2$ are each independently methyl or ethyl or $R^1$ and $R^2$ together with the carbon atom to which they are attached form a cyclohexyl ring.

31. The process of claim 30 wherein $R^3$ is a hydrogen atom, and $R^1$ and $R^2$ are each independently methyl or ethyl.

32. A process according to claims 1, 9 or 28, further comprising the step whereby the resulting chloroketoamine of formula (I) or (IA) may be reacted with an organic acid chloride of formula (IX) in the presence of a base to form a fungicidal amide compound of formula (X)

{ (I) or (IA) } + ZCOCl (IX) →[base]

22

-continued (X)

wherein

A is chloro or a hydrogen atom,

Z is alkyl or substituted alkyl, aryl or substituted aryl, heteroaryl or substituted heteroaryl or phenylene, R and $R^3$ are each independently a hydrogen atom or alkyl, and $R^1$ and $R^2$ are each independently an alkyl or substituted alkyl group, or $R^1$ and $R^2$ together with the carbon atom to which they are attached form a cyclic structure.

33. The process of claim 32 wherein

A is a hydrogen atom,

Z is $(C_1-C_8)$alkyl, phenyl or phenyl substituted with up to three substituents independently selected from the group consisting of halo, $(C_1-C_4)$alkyl, $(C_1-C_4)$alkoxy, $(C_2-C_6)$alkynyl, nitro and cyano, 2-naphthyl, 3-pyridyl and 1,4-phenylene, R is a hydrogen atom or a $(C_1-C_4)$alkyl, and $R^1$ and $R^2$ are each independently a $(C_1-C_4)$alkyl or $R^1$ and $R^2$ together with the carbon atom to which they are attached form a cyclopentyl or cyclohexyl ring.

34. The process of claim 33 wherein

Z is 3-heptyl, phenyl, 4-halophenyl, 2,6-dihalophenyl, 4-$(C_1-C_4)$alkylphenyl, 3,5-dihalophenyl, 3,5-di $(C_1-C_4)$alkylphenyl, 4-$(C_1-C_4)$alkyl-3,5-dihalophenyl, 4-cyano-3,5-dihalophenyl, 4-$(C_1-C_4)$alkoxy-3,5-dihalophenyl, 4-nitrophenyl, 2-naphthyl, 3-pyridyl or 1,4-phenylene, R and $R_3$ are each independently a hydrogen atom, methyl or ethyl, and $R^1$ and $R^2$ are each independently methyl or ethyl or $R^1$ and $R^2$ together with the carbon atom to which they are attached form a cyclohexyl ring.

35. The process of claim 34 wherein

Z is 4-chlorophenyl, 2,6-difluorophenyl, 3,5-dimethylphenyl, 3,5-dichloro-4-methylphenyl, 4-nitrophenyl, 1,4-phenylene, 2-naphthyl, 3-pyridyl or 3-heptyl, R and $R^3$ are each a hydrogen atom, and $R^1$ and $R^2$ are each independently methyl or ethyl.

* * * * *